United States Patent [19]

Umezawa et al.

[11] 3,963,579

[45] June 15, 1976

[54] MICROBIOLOGICAL PROCESS FOR THE PRODUCTION OF PEPSTATINS

[75] Inventors: Hamao Umezawa, Tokyo; Takaaki Aoyagi, Fujisawa; Akira Takamatsu, Yokohama; Taiji Inui, Chigasaki, all of Japan

[73] Assignee: Sanraku-Ocean Co., Ltd., Tokyo, Japan

[22] Filed: Oct. 10, 1974

[21] Appl. No.: 513,795

[30] Foreign Application Priority Data
Oct. 17, 1973  Japan.............................. 48-116665
Oct. 20, 1973  Japan.............................. 48-118404

[52] U.S. Cl................................................ 195/80 R
[51] Int. Cl.²......................................... C21D 13/06
[58] Field of Search.................. 195/80 R, 65, 66 R

[56] References Cited

UNITED STATES PATENTS

| | | | |
|---|---|---|---|
| 3,740,319 | 6/1973 | Umezawa et al.................. | 195/80 R |
| 3,869,347 | 3/1975 | Umezawa et al.................. | 195/80 R |

*Primary Examiner*—Lionel M. Shapiro
*Attorney, Agent, or Firm*—Frank J. Jordan

[57] ABSTRACT

A process for producing pepstatins by means of a microorganism belonging to Streptomyces and producing pepstatins, wherein at least one amino acid selected from the group consisting of L-leucine, L-valine, L-alanine, L-aspartic acid, L-glutamic acid, and L-lysine is added to the reaction medium, which also contains an energy source.

6 Claims, No Drawings

3,963,579

MICROBIOLOGICAL PROCESS FOR THE PRODUCTION OF PEPSTATINS

FIELD OF THE INVENTION

This invention relates to a microbiological process for the production of pepstatins and more particularly to a method for the microbiological production of pepstatins by means of a pepstatin-producing microorganism belonging to Streptomyces.

The microbiological process of the present invention includes the production of pepstatins both by fermentation and by a microbial enzyme system. The former involves a reaction medium comprising a cell-growth-promoting system in which the microorganism grows and produces pepstatins; and the latter involves a reaction medium comrpising a non-growing cell system in which no growth of the microorganism occurs and only the pepstatin-producing reaction takes place. The former medium contains energy sources for the growth of the microorganism and the production of pepstatins; the latter medium contains an energy source only for pepstatin formation.

BACKGROUND OF THE INVENTION

1. Prior Art

Pepstatins are pentapeptides having the following general formula:

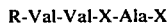

R-Val-Val-X-Ala-X wherein R stands for an acyl group, Val for L-valine, Ala for L-alanine, and X for $(CH_3)_2CH-CH_2-CH(NH_2)-CH(OH)-CH_2-COOH$, which are bound through amide linkages. The pepstatins include pepstatin A ($R=(CH_3)_2CH-CH_2-CO-$), pepstatin B ($R = CH_3-(CH_2)_4-CO-$), pepstatin C ($R = (CH_3)_2CH-(CH_2)_2-CO-$), and so on, according to the acyl group in the molecule. Pepstanone, in which the terminal X is $(CH_3)_2CH-CH_2-CH(NH_2)-CO-CH_3$, also belongs to this group.

Pepstatin was discovered by Umezawa et al. Similar substances were found by others later. These are all protease inhibitors produced by strains of Streptomyces and having high inhibitory activity on acid proteases, particularly on pepsin. It has been reported that pepstatin A takes effect on gastric ulcers clinically.

In Japanese Patent Publication 47-8996 and in U.S. Pat. No. 3,740,319 issued June 19, 1973, there is described and claimed a process for the production of a pepstatin characterized by cultivating a pepstatin-producing strain of Streptomyces such as *Streptomyces testaceus* MC144-Cl (ATCC 21469) or *Streptomyces argenteolus* var. *toyanakensis* MC210-Al (ATCC 21468) in a nutrient medium containing a carbon source such as glucose, starch or fat and a nitrogen source such a peptone, meat extracts, casein, soy bean meal or corn steep liquor under aerobic conditions.

The MC numbers are those assigned to the respective Streptomyces strains by the applicants themselves; and the ATCC numbers are those assigned to such strains by the American Type Culture Collection, in which these strains have been respectively deposited. The characteristics and other details of these two strains are set forth in the aforementioned U.S. Pat. No. 3,740,319, the disclosure of which is hereby fully incorporated in the present application by reference.

DESCRIPTION OF THE PREFERRED EMBODIMENTS

According to the present invention, it has been found that the addition of L-leucine to the reaction medium comprising the cell-growth-promoting system increases pepstatin accumulation remarkably and also that the co-addition of L-leucine and L-valine is more effective than the L-leucine addition alone. It has been further discovered that the addition of L-leucine provides a significant increase in pepstatin A production and raises the ratio of pepstatin A to the total pepstatins accumulated in the medium. It has been still further found that pepstatins are formed in a reaction medium comprising a non-growing cell system containing, for example, washed cells or cells treated as by freezing and thawing or by lyophylizing, which cells are obtained from a culture of a strain of Streptomyces producing pepstatins, when the above-mentioned amino acid or amino acids are added to the reaction medium.

It is an object of the present invention to provide an advantageous method for producing pepstatins microbiologically in high yields compared with previous methods.

Another object is to provide a method for producing pepstatin A specifically and obtaining a product with a high content of pepstatin A, in comparison to previous processes, wherein only a mixture of pepstatins such as pepstatin A, pepstatin B, pepstatin C, and so on is produced.

It is a still further object of the present invention to provide a method for producing pepstatins enzymatically in a solution having simpler constituents and obtaining pepstatins of high purity by simpler recovering processes.

Yet another object of this invention is to provide an industrially advantageous method for producing pepstatins, utilizing substrates for the formation of pepstatins efficiently without any metabolic waste of cell growth, because they are consumed by the cells not for their growth but only for pepstatin production.

Still another object is the provision of an enzymatic method for making pepstatins by a continuous process with insoluble enzymes.

As described above, the present invention is principally concerned with a process for producing pepstatins by contacting a pepstatin-producing Streptomyces with L-leucine and other amino acids in a reaction medium containing energy sources for cell growth and pepstatin production or energy sources only for pepstatin formation. This contact or reaction of the pepstatin-producing Streptomyces with L-leucine and other amino acids may be performed in a growth system, that is, in a system containing growing cells of the Streptomyces, and may be also conducted in a non-growth system, that is, in a system containing non-growing cells, washed cells, frozen cells, lyophilized cells or the like. The process for producing pepstatins in the growth system, or the fermentative process, comprises cultivating the pepstatin-producing Streptomyces in a cell-growth-promoting system containing L-leucine or L-leucine and L-valine, together with the energy sources for cell growth and pepstatin formation, wherein the microorganism grows and produces pepstatins. Similarly, the process for the production of pepstatins in the non-growth system, or the enzymatic process, includes the initial cultivation of the pepstatin-producing Streptomyces in a nutrient medium and the reaction of the cells obtained from the resulting culture with at least one amino acid selected from the group consisting of L-leucine, L-valine, L-alanine, L-aspartic acid, L-glutamic acid, and L-lysine in the non-growing cell system, wherein no cell growth takes place.

Experiments 1 to 3 illustrate the method for producing pepstatins in the growth system.

The pepstatins were assayed in carrying out this invention according to the following method: A mixture of 1 ml of 0.6% highly purified casein dissolved in 0.08M lactate buffer solution, pH 2.2, 0.7 ml of 0.02M KCl-HCl buffer solution, pH 2.0, and 0.2ml of pepstatin solution was incubated at 37° for 3 min. To this mixture 4mcg of pepsin (SIGMA, 2XCRY) dissolved in 0.1ml of 0.02M KCl-HCl buffer solution were added. The mixture was incubated at 37° for 30 min. The reaction was stopped by the addition of 2.0ml of 1.7M perchloric acid. After 1 hr at room temperature, the optical density (a) of the supernatant liquid was read at 280m$\mu$. A inhibition rate was obtained according to:

$$\frac{(b) - (a)}{(b)} \times 100$$

where (b) is the optical density at 280m$\mu$ of the tube without the pepstatins. The amounts of the pepstatins were calculated from a standard curve obtained by plotting the known concentrations of the pepstatins and the inhibition rates.

Pepstatin A was assayed as follows: Crude or purified pepstatin powder was obtained according to the method described by Umezawa et al. A certain amount of the powder was hydrolyzed in 6N HCl at 105° – 110° for 17 hours. Isovaleric acid in an ether extract of the hydrolysate was measured by gas chromatography. The pepstatin A content in total Pepstatins (%) was obtained from the following equation:

$$\frac{\text{Isovaleric acid (\%)}}{\text{Pepstatins (\%)}} \times \frac{685.88}{102.13} \times 100$$

Experiment 1

Table 1 shows the respective effects of various amino acids added to the reaction medium upon the pepstatin formation and the ratio of pepstatin A to the total pepstatins accumulated. In this experiment *Streptomyces testaceus* MC144-Cl (ATCC 21469) was added to a 50ml portion of a basal medium, pH7.2, sterilized at 120° for 15 min and containing 1.0% glucose, 1.0% starch, 0.75% polypeptone, 0.75% Ehrlich meat extracts, 0.3% NaCl, 0.01% MgSO$_4$.7H$_2$O, 0.1% KH$_2$PO$_4$ and 0.1% metal ions solution consisting of 0.7% CuSO$_4$.5H$_2$O, 0.1% FeSO$_4$.7H$_2$O, 0.8% MnCl$_2$.4H$_2$O and 0.2% ZnSO$_4$.7H$_2$O, to which each amino acid in Table 1 was added at a concentration of 0.3%. The fermentation was carried out at 28° with shaking at 220 r.p.m. for 4 days.

Table 1

| L-Amino Acid. | Pepstatins Produced mcg/ml | Pepstatin A Content % |
|---|---|---|
| Aspartic acid | 93 | 47 |
| Alanine | 76 | 54 |
| Arginine | 60 | 39 |
| Isoleucine | 160 | 61 |
| Glycine | 100 | 37 |
| Glutamic acid | 85 | 55 |

Table 1-continued

| L-Amino Acid. | Pepstatins Produced mcg/ml | Pepstatin A Content % |
|---|---|---|
| Cysteine | 54 | 48 |
| Threonine | 54 | 51 |
| Serine | 40 | — |
| Tyrosin | 85 | 45 |
| Valine | 380 | 40 |
| Histidine | 20 | — |
| Phenylalanine | 110 | 52 |
| Proline | 120 | 60 |
| Methionine | 150 | 43 |
| Lysine | 130 | 50 |
| Leucine | 520 | 78 |
| No addition | 130 | 52 |

Experiment 2

This experiment was carried out in the same manner as in Experiment 1 except that *Streptomyces argenteolus* var. *toyonakensis* MC210-Al (ATCC 21468) was used. The amount of pepstatins produced and the pepstatin A content of the flasks containing L-leucine, L-valine and the control were 210 mcg/ml: 69%, 128 mcg/ml: 53%, and 83 mcg/ml: 44%, respectively.

Experiment 3

In this experiment the effect of the concentration of these two amino acids on pepstatin formation was examined. To the same basal medium as described in Experiment 1, L-leucine and L-valine were added at various concentrations as indicated in Table 2. The fermentation was conducted under the same conditions as in Experiment 1. Table 2 shows that the increase of pepstatin formation depends upon the concentration of L-leucine and that L-valine augments the effect of L-leucine. Concentrations of L-leucine and L-valine up to 2–5% are generally effective; and the ratio of the two amino acids is preferably 0.5 – 2 : 1.

Table 2

| L-Leucine % | L-Valine % | Pepstatins Produced mcg/ml | Pepstatin A Content % |
|---|---|---|---|
| — | — | 155 | 57 |
| 0.1 | — | 353 | 72 |
| 0.3 | — | 800 | 79 |
| 0.5 | — | 1050 | 68 |
| — | 0.1 | 152 | 53 |
| — | 0.3 | 340 | 46 |
| — | 0.5 | 560 | 49 |
| 0.05 | 0.05 | 490 | 70 |
| 0.15 | 0.15 | 1190 | 83 |
| 0.25 | 0.25 | 1710 | 77 |

These three experiments clearly show that the addition of L-leucine or L-valine increases the formation of pepstatins and that L-leucine is highly effective for the production of pepstatins and especially pepstatin A.

The next four experiments are concerned with the method for the production of pepstatins in the non-growth system.

Experiment 4

Table 3 shows the enzymatic formation of pepstatins from L-leucine and other reactants. In this experiment a medium containing 1.0% glucose, 1.0% starch, 0.75% polypeptone, 0.75% Ehrlich meat extracts, 0.3% NaCl, 0.01% MgSO$_4$.7H$_2$O, 0.1% KH$_2$PO$_4$ and 0.1% metal ions solution (the same composition as described in Experiment 1), pH 7.2, was prepared and sterilized at 120° for 15 min. A pepstatin-producing strain *Streptomyces testaceus* MC144-Cl (ATCC 21469) was added to a 50 ml portion of the medium in a 500 ml flask. The flask was shaken on a rotary shaker (220 r.p.m.) at 28° for 48 hrs. The cells were harvested, washed with cold sterile water three times, and suspended in M/15 phosphate buffer solution, pH 7.0. 100ml flasks containing 20ml of a reaction mixture consisting of L-leucine and other reactants as indicated in Table 3, the cell suspension (final concentration = 10mg/ml as dry matter), and 10 mcg/ml of chloroamphenicol were shaken on a rotary shaker at 28° for 20 hrs. Chloramphenicol is added to prevent contamination and growth of the cells during the reaction because the strains employed in these experiments were sensitive to antibiotics such as chloramphenicol, erythromycin or tetracyclin. The results shown in Table 3 indicate that significant amounts of pepstatins were formed by the aerobic reaction of L-leucine and the cells, and that the amounts of the product were increased by the addition of amino acids such as L-valine, L-lysine, L-aspartic acid, or L-alanine, of sugars such as glucose, of organic acids such as malic acid, or of alcohols such as glycerine. Similar results (Table 4) were obtained when the reaction was carried out with the organic acids related to the Krebs cycle such as citric acid, succinic acid, pyruvic acid, glutamic acid, or alpha-ketoglutaric acid in place of malic acid in the present experiment; the glucose could also be replaced by sucrose, invert sugar, molasses, or starch hydrolysate.

Table 3

| Composition of Reaction Mixture | | Pepstatins Produced (mcg/ml) |
|---|---|---|
| L-Leucine | 0.1% | 256 |
| L-Leucine | 0.1% | 300 |
| L-Valine | 0.1% | |
| L-leucine | 0.1% | 304 |
| L-Lysine | 0.1% | |
| L-Leucine | 0.1% | 318 |
| L-Aspartic acid | 0.1% | |
| L-Leucine | 0.1% | 310 |
| L-Alanine | 0.1% | |
| L-Leucine | 0.1% | 330 |
| L-Valine | 0.1% | |
| L-Alanine | 0.1% | |
| L-Leucine | 0.1% | 410 |
| Glucose | 2.0% | |
| L-Leucine | 0.1% | 760 |
| L-Valine | 0.1% | |
| Glucose | 2.0% | |
| L-Leucine | 0.1% | 840 |
| L-Valine | 0.1% | |
| L-Alanine | 0.1% | |
| Glucose | 2.0% | |
| L-Leucine | 0.1% | 336 |
| Malic acid | 1.3% | |
| L-Leucine | 0.1% | 420 |
| L-Valine | 0.1% | |
| L-Alanine | 0.1% | |
| Malic acid | 1.3% | |
| L-Leucine | 0.1% | 360 |
| Glycerine | 2.0% | |
| Control | | 52 |

Table 4

| Composition of Reaction Mixture | | Pepstatins Produced (mcg/ml) |
|---|---|---|
| L-Leucine | 0.1% | 374 |
| Citric acid | 1.3% | |
| L-Leucine | 0.1% | 362 |
| Succinic acid | 1.0% | |
| L-Leucine | 0.1% | 327 |
| Pyruvic acid | 1.0% | |
| L-Leucine | 0.1% | 375 |
| L-Glutamic acid | 0.1% | |
| L-Leucine | 0.1% | 320 |

Table 4-continued

| Composition of Reaction Mixture | | Pepstatins Produced (mcg/ml) |
|---|---|---|
| γ-Ketoglutaric acid | 1.0% | |
| L-Leucine | 0.1% | 532 |
| Citric acid | 1.3% | |
| L-Valine | 0.1% | |
| L-Leucine | 0.1% | 405 |
| Sucrose | 2.0% | |
| L-Leucine | 0.1% | 372 |
| Invert sugar | 2.0% | |
| L-Leucine | 0.1% | 343 |
| Molasses (T.S. 55%) | 2.0% | |
| L-Leucine | 0.1% | 337 |
| Starch hydrolysate (T.S. 55%) | 2.0% | |
| L-Leucine | 0.1% | 485 |
| Glucose | 2.0% | |
| Citric acid | 1.3% | |

Experiment 5

Cell suspensions were prepared in the same manner as described above except for harvesting the cells after the cultivation times as indicated in Table 5. 20ml of a reaction mixture containing 2% glucose, 0.1% L-leucine, 0.1% L-valine, the cell suspension (final concentration = 10mg/ml as dry matter), and 10mcg/ml chloramphenicol for the same purpose as described above were incubated in a 100ml flask on a rotary shaker at 28° for 20 hrs. The amounts of pepstatins produced are given in Table 5, which indicates that the cells harvested after 48 hrs, at the logarithmic growth plate, showed the highest activity for the production of pepstatins.

Table 5

| Time (hr) | Weight of Dry Cells (g/100ml of Broth) | Pepstatins Produced (mcg/ml) | Specific Activity (Pepstatins, mcg/dry cell,mg) |
|---|---|---|---|
| 24 | 0.48 | 277 | 27.7 |
| 48 | 0.75 | 855 | 85.5 |
| 72 | 1.09 | 385 | 38.5 |
| 96 | 1.00 | 0 | 0 |

Experiment 6

Cells cultivated for 48 hrs were obtained as described above and suspended in buffer solutions having various pH values as indicated in Table 6. 20 ml of a reaction mixture containing 0.1% L-leucine, 0.1% L-valine, 2% glucose, 10 mcg/ml chloroamphenicol, and the cell suspension (final concentration = 10 mg/ml as dry matter) were inccubated in a 100ml flask on a rotary shaker at 28° for 20 hrs. The amounts of pepstatins produced in the mixture are shown in Table 6. The pepstatin formation takes place between a pH of 6 and 7, the optimum pH being 6.5.

Table 6

| Initial pH | Buffer Solution | Final pH | Pepstatins Produced (mcg/ml) |
|---|---|---|---|
| 3.0 | McIlvaine's | 3.1 | 0 |
| 4.0 | McIlvaine's | 4.0 | 0 |
| 5.0 | Phosphate | 5.0 | Trace |
| 6.0 | Phosphate | 6.1 | 150 |
| 6.5 | Phosphate | 6.7 | 820 |
| 7.0 | Phosphate | 7.3 | 230 |
| 8.0 | Phosphate | 8.0 | Trace |
| 9.0 | Phosphate (NaOH) | 8.8 | 0 |

Experiment 7

Cells cultivated for 48 hrs were obtained as described above; and three kinds of enzyme preparations were made as follows: (1) the cells were suspended in 1/5 culture broth volume of sterile water, frozen in a freezer and thawed. (2) The cells were suspended in a sterile stabilizer solution containing 5% skim milk and 2% sodium glutamate and lyophilized. (3) The cells were used for the following reaction without any treatment. Malic acid or glucose was added to a mixture containing 0.1% L-leucine, 0.1% L-valine, 0.1% L-alanine, and 100mcg/ml chloramphenicol, at a concentration of 1.3% or 2%, respectively. The mixture was incubated with the cell preparations mentioned above at the concentration of 10 mg/ml as dry matter as indicted in Table 7 under the conditions of Experiment 4. The results are given in Table 7. The frozen and thawed cells and the lyophilized cells provided significant activity of pepstatin formation as well as the washed cells, of which the activity was high as already stated above.

Table 7

| Cells | Pepstatins Produced (mcg/ml) | |
|---|---|---|
| | Malic Acid | Glucose |
| Frozen and thawed | 348 | 850 |
| Lyophilized | 226 | 692 |
| Washed (No treatment) | 420 | 1025 |

The results obtained from Experiments 4 – 7 clearly show that pepstatins are effectively produced from L-leucine in the non-growth system and that the presence of other amino acids, sugars, organic acids and alcohol provides more satisfactory results. Several industrial productions utilizing microbial cells as enzymes or enzyme systems have been already known, in which the reactions of the processes are usually one-step reactions such as hydrolysis or transformation. The process of the present invention, however, is very unique because the reaction involves the synthesis of a physiologically active compound consisting of three amino acids and one acyl group from simple starting materials by multiple steps, not by fermentation accompanying cell growth but by an enzyme system.

In accordance with the present invention, pepstatins are advantageously produced in the growth system in which L-leucine or L-leucine and L-valine are present and the pepstatin-producing microorganism grows, producing pepstatins, especially pepstatin A, effectively. In the non-growth system, pepstatins are produced from L-leucine or L-leucine and at least one reactant selected from the group consisting of amino acids including L-valine, L-alanine, L-aspartic acid, L-glutamic acid, and L-lysine, sugars, organic acids and alcohols by the cells of the pepstatin-producing microorganism without any cell growth.

In carrying out the present invention, the particular microorganism employed is Streptomyces strain producing pepstatins. The typical strains are *Streptomyces testaceus* and *Streptomyces argenteolus* var. *toyonakensis* as mentioned above. Several other strains have been also reported as the microorganisms capable of producing pepstatins, and such microorganisms may be further isolated. It is well known that spontaneous and artifical mutants of Streptomyces are often isolated. The microorganisms employed in this invention include the species of Streptomyces, the mutants thereof, and the strains indistinguishable therefrom which are capable of producing pepstatins.

The media used in the growth system for carrying out the method of the present invention fermentatively are the nutrient media known as suitable for growth of Streptomyces. As the carbon source any of those carbohydrotes may be used which are normally employed in fermentation such as glycerine, glucose, maltose, sucrose, starch, molasses and the like. The nitrogen may be furnished by any of those materials which are usually used such as peptone, meat extracts, corn steep liquor, cotton seed meal, peanut meal, soy bean meal, yeast extracts, NZ-amine, casein, sodium nitrate, ammonium nitrate, ammonium sulfate and the like. The media may contain inorganic salts such as sodium chloride, potassium phosphate, magnesium sulfate, calcium carbonate and the like and may also contain trace elements such as a cupric salt, a ferrous salt, or a manganese salt if necessary. The same media for the growth system described above may be used as the nutrient media for cultivating the microorganism to obtain the cells in carrying out the present invention enzymatically.

L-Leucine and L-valine added to the growth system medium in the method of this invention may be used in the form of pure crystals, crude powder or concentrated solutions obtained by known methods from the hydrolysate of protein or from the broth of amino acid fermentation. Salts and esters thereof may be also used and are meant to be included by the term "amino acids" as used herein. These amino acids are preferably added to the fermentation after initial growth of the microorganism has been started, for example, after 20–50 hours, or may be added in parts periodically during the fermentation; but they may also be added at the start of the fermentation. The total amounts of L-leucine and L-valine to be added or a part of each may be added in the seed culture of the fermentation as will appear from the examples set forth hereafter.

The fermentation should be conducted under aerobic conditions. A rotary or reciprocal shaker is used in the laboratory, but a submerged culture in a fermentor equipped with an agitator and an air inlet is suitable for production on an industrial scale. The cultivation may be carried out at the temperature and the pH which are usually employed for the growth of the microorganisms and for pepstatin production.

The initial pH of the cultivation is preferably maintained between 5 and 8, and the temperature between 25° and 35°. Shaking of a culture in a flask is performed for a period from 3 to 8 days, and culture times of 40–120 hours give highly satisfactory results in the case of a fermentor. In order to obtain the cells for conducting the method of the present invention enzymatically, the cultivation of the above-mentioned microorganism is carried out in almost the same manner as in the fermentation process, but the microorganism is preferably grown until the highest specific activity of the cells, or the highest pepstatin producing activity per cell, is obtained. Usually the maximum of such activity appears at the logarithmic growth phase, for example, 30–50 hours after inoculation when the microorganism is cultivated under the above-mentioned conditions.

Cells harvested by centrifugation or filtration may be used immediately without any treatment; but, if necessary, they may also be used after washing with water, physiological saline solution, or suitable buffer solution, for example, an M/100 – M/5 phosphate buffer solution (pH 5–7). The cells may also be suspended in water and frozen or lyophilized with skim milk or sodium glutamate as a stabilizer. Thus treated cells are usually preservable. The techniques of insolubilization of cells recently developed may also be employed. The amounts of the cells or the treated cells used in the method of this invention are generally around 0.5g as dry matter, at most 5g, per 100ml of the reaction mixture, which will vary depending upon the strains used, the cultural conditions, the kind of cell preparation, the specific activity of the cell preparation, and the conditions of the reaction.

The medium for the non-growth system, or the reaction mixture, contains L-leucine or L-leucine and at least one reactant selected from the group consisting of various amino acids, sugars, organic acids and alcohols. The reaction for the production of pepstatins takes place in the solution containing L-leucine only; but goods results are obtained by adding at least one reactant selected from the group consisting of various amino acids, sugars, organic acids, alcohols and the materials containing such substances to the solution containing the L-leucine. The amino acids other than L-leucine which are preferred for use as the reactants are L-valine, L-alanine, L-aspartic acid, L-glutamic acid and L-lysine.

The amounts of L-leucine and the amino acid added as the reactant are desirably 0.01 – 1% although the preferred concentration will vary, depending upon the strains employed, the kind of cell preparation, and the conditions of the pepstatin-producing reaction. Materials containing amino acids such as peptone, casamino acids, or corn steep liquor may be used industrially. The preferred amounts of these materials are generally 1 – 10%. Sugars which are preferred for use in this process are glucose, fructose, sucrose, maltose, sugar phosphates such as glucose-6-phosphate, invert sugar, or materials containing sugars such as molasses or starch hydrolysate. As the organic acids used in this invention, those which are related to the Krebs cycle such as citric acid, malic acid, succinic acid, pyruvic acid, or alpha-ketoglutaric acid give good results. Glycerine, propylene glycol, or their phosphates are suitable as the alcohols used in the method of the present invention. These sugars or organic acids are preferably added at a concentration of 0.1 – 3%. Satisfactory results are obtained by adding L-leucine, other amino acids, and at least one reactant selected from the group consisting of sugars, organic acids, and alcohols.

The production of the pepstatins is performed in aqueous solution, and desirably a buffer solution is used because the formation of pepstatins depends upon the pH of the reaction mixture. Phosphate buffer solutions of a final concentration of M/100 – M/5, for example, give good resullts. The pH of the reaction mixture is generally adjusted between 5 and 8 and desirably between 6 and 7. The reaction is carried out at a temperature between 20° and 40°, and preferably between 25° and 35°. The pH and the temperature will vary, depending upon the strain employed.

In carrying out the present invention enzymatically, a rotary or reciprocal shaker is suitable for the aerobic reaction in the laboratory. A reactor equipped with an agitator and an air inlet may be used in large-scale production. The reaction is conducted for a period of from 10 to 30 hours, which will also vary depending upon the strain employed, the kind of cell preparation, and the conditions of the reaction. Usually no cell growth occurs during the reaction. In order to prevent the growth of the cells added as well as contamination, an antibiotic to which the strain employed is sensitive such as chloramphenicol, erythromycin or tetracyclin may be used at very low concentration, for example, 10 mcg/ml.

The pepstatins produced fermentatively and enzymatically according to the method of the present invention may be recovered from the broth, the reaction mixture, the filtrate, or the solid material containing cells in high yields by means of extraction with organic solvents such as methanol, n-butanol, or dimethylsulfoxide, or of chromatography with active carbon, ion exchange resins, alumina, or silica gel. The pepstatins produced enzymatically by the method of this invention are easily recovered in good yields and high purity by comparatively simple procedures because the pepstatins are formed in a solution containing fewer constituents at lower concentrations than in the fermentation broth.

The following examples illustrate methods of carrying out the present invention, but it is to be understood that they are given for purpose of illustration and not of limitation:

EXAMPLE 1

A medium having the following composition was prepared:

| | Percent (weight) |
|---|---|
| Glucose | 3 |
| Polypeptone | 3 |
| NaCl | 0.3 |
| K$_2$HPO$_4$ | 0.1 |
| MgSO$_4$.7H$_2$O | 0.1 |
| Yeast extracts | 0.3 |
| *Metal ions solution | 0.1 |

*The composition is given above in Experiment 1.

A series of 500ml shaker flasks each containing 50ml of the medium, of which the first flask contained 0.3% L-leucine, the second, 0.3% L-valine, the third, 0.3% L-leucine and 0.3% L-valine, and the fourth was the control, were inoculated after sterilization at 120° for 15 minutes with a culture of Streptomyces testaceus MC144-C1 (ATCC 21469). The flasks were shaken on a reciprocal shaker (150 r.p.m.) at 28° for 6 days. Table 8 shows the pH and the pepstatins produced. The broth was extracted with two equal volumes of n-butanol. The extracts were evaporated to dryness in vacuo to obtain brown powders. The yields were 4.7g, 2.7g, 10.6g, and 1.1g from 1000ml of the broths from the flasks containing L-leucine, L-valine, L-leucine and L-valine, and the control, respectively. The amounts of these powders necessary for 50% inhibition (ID$_{50}$) of pepsin were 0.14mcg, 0.15mcg, 0.12mcg, and 0.18mcg, respectively.

Table 8

|  | pH Initial | pH 6 Days | Pepstatins Produced (mcg/ml) | Pepstatin A Content (%) |
|---|---|---|---|---|
| L-Leucine | 6.8 | 7.6 | 724 | 80.3 |
| L-Valine | 6.8 | 7.7 | 380 | 58.4 |
| L-Leucine and L-Valine | 6.8 | 7.5 | 1950 | 77.6 |
| Control (No Addition) | 6.8 | 7.8 | 132 | 61.2 |

EXAMPLE 2

Crude L-leucine (purity = 78.2%) obtained from the hydrolysate of soy bean protein and crude L-valine (purity = 87.3%) obtained from the broth of L-valine fermentation were added to the same medium at a concentration of 0.5% in the same manner as in Example 1. The flasks were inoculated with a high potency strain of *Streptomyces argenteolus* var. *toyonakensis* MC210-A1 (ATCC 21468) and the fermentation was conducted under the conditions of Example 1. The results are set forth in Table 9.

Table 9

|  | pH Initial | pH 6 Days | Pepstatins Produced (mcg/ml) | Pepstatin A Content (%) |
|---|---|---|---|---|
| Crude L-Leucine | 7.0 | 7.8 | 563 | 65.1 |
| Crude L-Valine | 7.0 | 7.7 | 341 | 55.2 |
| Crude L-Leucine and Crude L-Valine | 7.0 | 7.4 | 1244 | 71.9 |
| Control (No Addition) | 7.0 | 8.0 | 102 | 48.3 |

EXAMPLE 3

A medium having the following composition was prepared:

|  | Percent (weight) |
|---|---|
| Glucose | 2 |
| Starch | 1 |
| Soy bean meal | 2 |
| Corn steep liquor | 1 |
| Yeast extracts | 0.3 |
| $K_2HPO_4$ | 0.1 |
| $MgSO_4 \cdot 7H_2O$ | 0.1 |
| Metal ions solution | 0.05  pH 6.8 |

Ten liters each of the medium in four 20-liter jar fermentors were sterilized at 115° for 20min and inoculated with 200ml of a seed culture of a high potency strain of *Streptomyces testaceus* MC144-C1 (ATCC 21469) grown by rotary shaking at 28° for 48hrs. The fermentation was carried out at 28° with agitation (340r.p.m.) and aeration (5l/min). After 48hrs, a suspension of 50g of L-leucine, 50g of L-valine or 30g of L-leucine and 20g of L-valine was aseptically added to each jar fermentor, respectively. The fermentation was continued up to 96hrs. The broth filtrate (5l) was treated with active carbon and extracted with n-butanol. The extracts were evaporated to dryness in vacuo to obtain brown powders. The crude powder was dissolved in water and adsorbed onto an active carbon column. The active fractions eluted with methanol were pooled and dried in vacuo to yield white powder. Table 10 shows the results.

When 0.5% each of L-leucine and L-valine were added to the seed culture and the remainders were added to the fermentation in the same manner as described above, the results were more satisfactory.

Table 10

|  | pH | Pepstatins Produced (mcg/ml) | White powder Yields (g/5 l) | White powder $ID_{50}$ (mcg) | White powder Pepstatin A Content (%) |
|---|---|---|---|---|---|
| L-Leucine | 7.1 | 1390 | 16.2 | 0.054 | 71.9 |
| L-Valine | 7.6 | 810 | 9.8 | 0.057 | 60.4 |
| L-Leucine and L-Valine | 7.3 | 2120 | 25.0 | 0.053 | 75.8 |
| Control (No Addition) | 7.7 | 172 | 2.1 | 0.060 | 62.3 |

EXAMPLE 4

A fermentation medium having the following composition was prepared:

|  | Percent (weight) |
|---|---|
| Glucose | 5 |
| Polypeptone | 3 |
| Corn gluten meal | 2 |
| Yeast extracts | 0.2 |
| $K_2HPO_4$ | 0.1 |
| $MgSO_4 \cdot 7H_2O$ | 0.1 |
| Metal ions solution | 0.05  pH 6.8 |

Ten liters of the medium in a 20 liter fermentor, after L-leucine and L-valine were added as indicated in Table 11, were sterilized at 115° for 20 min and inoculated with 200ml of a growing culture of a high potency strain of *Streptomyces testaceus* MC144-C1 (ATCC 21469). The fermentation was carried out at 30° with agitation (340 R.P.M.) and aeration (5l/min). The results are given in Table 11.

Table 11

| No. | L-Leucine (%) | L-Valine (%) | Pepstatins Produced (mcg/ml) | Pepstatin A Content (%) |
|---|---|---|---|---|
| 1 | — | — | 140 | 58.4 |
| 2 | 0.2 | 0.2 | 880 | 69.3 |
| 3 | 0.4 | 0.4 | 2380 | 68.8 |
| 4 | 0.6 | 0.6 | 3220 | 70.1 |
| 5 | 0.8 | 0.8 | 4550 | 75.9 |
| 6 | 1.0 | 1.0 | 4780 | 71.3 |
| 7 | 1.5 | 1.5 | 6400 | 73.2 |
| 8 | 2.0 | 2.0 | 8300 | 70.5 |
| 9 | 2.5 | 2.5 | 9800 | 71.5 |
| 10 | 3.0 | 3.0 | 9850 | 72.3 |

EXAMPLE 5

A medium having the following composition was prepared:

| | Percent (weight) | |
|---|---|---|
| Glucose | 2 | |
| Polypeptone | 2 | |
| Yeast extracts | 0.3 | |
| NaCl | 0.3 | |
| KH$_2$PO$_4$ | 0.1 | |
| MgSO$_4$.7H$_2$O | 0.1 | pH 6.8 |

A 500ml flask containing 50 ml of the medium was sterilized at 120° for 15 min and inoculated with Streptomyces testaceus MC144-C1 (ATCC 21469). The flask was shaken on a reciprocal shaker at 150 r.p.m. at 28° for 48 hrs. The cells were harvested by centrifugation and washed with cold sterile water twice. A reaction mixture containing 2g of glucose, 0.2g of L-leucine, 0.1g of L-valine, 0.18g of L-alanine, 1 mg of chloramphenicol, 500mg of the cells (as dry matter), and M/15 phosphate buffer in the total volume of 100ml was shaken for 20 hrs under the conditions of the cell culture mentioned above.

The filtrate of the reaction mixture was extracted with two equal volumes of n-butanol. Evaporation to dryness of the combined n-butanol layer gave 650mg of a brownish crude powder of pepstatins. The ID$_{50}$ of the crude powder was 0.091 mcg.

EXAMPLE 6

Streptomyces argenteolus var. toyonakensis MC210-A1 (ATCC 21468) was added to the medium having the same composition as in Example 5 and cultivated, shaking on a rotary shaker at 220 r.p.m. at 28° for 50 hrs. The cells harvested by centrifugation were washed with cold physiological saline twice and suspended in a sterile solution containing 5% skim milk and 2% sodium glutamate and then lyophilized. 10 ml of a solution containing 0.2% L-leucine, 0.2% L-valine, 0.2% L-alanine, 2% fructose and M/10 phosphate buffer (pH 6.8) was incubated with 100mg of the lyophilized cells in a 100ml flask on a rotary shaker at 220 r.p.m. at 30° for 24 hrs.

The concentration of the pepstatins produced in the reaction mixture was 1010 mcg/ml.

EXAMPLE 7

A 20 liter fermentor containing 10 liters of a medium sterilized at 115° for 20min and having the following composition:

| | Percent (weight) | |
|---|---|---|
| Glucose | 1 | |
| Starch | 1 | |
| Corn gluten meal | 1 | |
| Corn steep liquor | 1 | |
| Yeast extracts | 0.3 | |
| KH$_2$PO$_4$ | 0.1 | |
| MgSO$_4$.7H$_2$O | 0.1 | |
| Metal ions solution | 0.1 | pH 7.0 | was inoculated with 200ml of a seed culture of a high potency strain of Streptomyces testaceus MC144-C1 (ATCC 21469). The cultivation was conducted at 28° for 40 hrs with agitation (340 r.p.m.) and aeration (5 liter/min). The cells harvested by centrifugation were washed with cold physiological saline water twice and frozen at −30°. Five liters of a solution sterilized at 105° for 5 min and contacting 0.3% L-leucine, 3% peptone and M/15 phosphate buffer (pH 6.5) were incubated with the whole amounts of the frozen cells obtained above in a 10 liter fermentor at 28° for 24 hrs with agitation (200 r.p.m.) and aeration (2.5 liter/min).

The pepstatins thus produced were extracted with n-butanol from the filtrate of the reaction mixture after active carbon treatment. The brownish powder obtained by evaporation to dryness of the n-butanol extracts was dissolved in water and applied to active carbon chromatography. Fractions having anti-pepsin activity eluted with aqueous methanol were combined. Evaporation in vacuo of the combined fractions gave 23.6g of a white powder, of which the ID$_{50}$ was 0.047 mcg.

All temperatures indicated in the specification and claims are Centigrade.

It is thought that the invention and many of its attendant advantages will be understood from the foregoing description and that it will be apparent that various changes may be made in the form, construction, and arrangements of the parts without departing from the spirit and scope of the invention or sacrificing all of its material advantages. The form heretofore described being merely a preferred embodiment thereof.

What is claimed is:

1. A process for producing pepstatins having a high content of pepstatin A, which comprises adding at least one member selected from the group consisting of L-leucine plus L-valine, their salts and their esters in the form of pure crystals, crude powder or concentrated solution thereof to a reaction medium comprising a cell growth-promoting system containing a pepstatin-producing microorganism belonging to Streptomyces and also containing an energy source, said at least one member being added to the reaction medium in a total amount of 0.6 to 6.0% of the medium and in a ratio of L-leucine, its salts and its esters to L-valine, its salts and its esters of 0.5 : 1 to 2 : 1 based upon the calculation thereof as free acid, cultivating said microorganism in said reaction medium at a pH between 5 and 8 under aerobic conditions at a temperature between 25° and 35°C whereby pepstatins are produced, and recovering the resulting pepstatins from said reaction medium.

2. A process according to claim 1, in which said microorganism is selected from the group consisting of Streptomyces testaceus MC144-C1 (ATCC 21469) and Streptomyces argenteolus var. toyonakensis MC210-A1 (ATCC 21468).

3. A process for producing pepstatins having a high content of pepstatin A which comprises adding at least one member selected from the group consisting of L-leucine plus L-valine, their salts and their esters in the form of pure crystals, crude powder or concentrated solution thereof to a reaction medium comprising a non-growing cell system containing non-growing cells of a pepstatin-producing microorganism belonging to Streptomyces and also containing an energy source, said at least one member being added to the reaction medium in a total amount of 0.2 to 1.0% of the medium and in a ratio of L-leucine, its salts and its esters to L-valine, its salts and its esters of 0.5 : 1 to 2 : 1 based upon the calculation thereof as free acid, maintaining said reaction medium at a pH between 5 and 8 under aerobic conditions at a temperature between 20° and 40°C.

4. A process according to claim 3, in which said microorganism is selected from the group consisting of Streptomyces testaceus MC144-C1 (ATCC 21469) and

*Streptomyces argenteolus* var. *toyonakensis* MC210-A1 (ATCC 21468).

5. A process according to claim 3, in which at least one antibiotic selected from the group consisting of chloramphenicol, erythromycin and tetracyclin is added to said reaction system in order to prevent contamination by undesirable microbes.

6. A process according to claim 3, in which the energy source comprises at least one member selected from the group consisting of glucose, sucrose, invert sugar, molasses, starch hydrolysate, glycerine, malic acid, $\alpha$-ketoglutaric acid, glutamic acid, L-lysine, L-aspartic acid and L-alanine.

* * * * *